(12) United States Patent
Chang et al.

(10) Patent No.: US 12,383,138 B2
(45) Date of Patent: Aug. 12, 2025

(54) PHYSIOLOGICAL INFORMATION MONITORING AND IDENTIFICATION METHOD, CHARACTERIZATION INFORMATION MONITORING AND IDENTIFICATION METHOD, AND PHYSIOLOGICAL INFORMATION MONITORING RADAR

(71) Applicant: Wistron Corporation, New Taipei (TW)

(72) Inventors: Yao-Tsung Chang, New Taipei (TW); Yin-Yu Chen, New Taipei (TW); Chuan-Yen Kao, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 469 days.

(21) Appl. No.: 17/368,100

(22) Filed: Jul. 6, 2021

(65) Prior Publication Data
US 2022/0296099 A1    Sep. 22, 2022

(30) Foreign Application Priority Data

Mar. 17, 2021 (TW) .................................. 110109487
Mar. 17, 2021 (TW) .................................. 110109639

(51) Int. Cl.
*A61B 5/00* (2006.01)
*G01S 7/35* (2006.01)
(Continued)

(52) U.S. Cl.
CPC .......... *A61B 5/0015* (2013.01); *A61B 5/0004* (2013.01); *A61B 5/7257* (2013.01);
(Continued)

(58) Field of Classification Search
CPC ... A61B 5/0015; A61B 5/0004; A61B 5/7257; G01S 7/356; G01S 7/412; G01S 13/584;
(Continued)

(56) References Cited

U.S. PATENT DOCUMENTS 4,155,087 A * 5/1979 Okrent .................... G01S 13/78
714/824
4,292,637 A   9/1981 Johnson
(Continued)

FOREIGN PATENT DOCUMENTS

CN    108700645 A    10/2018
CN    111932826 A    11/2020
(Continued)

OTHER PUBLICATIONS

EESR dated Feb. 18, 2022, listed in related European patent application No. 21 190 299.4.
(Continued)

*Primary Examiner* — Olumide Ajibade Akonai
(74) *Attorney, Agent, or Firm* — McClure, Qualey & Rodack, LLP

(57) ABSTRACT

A monitoring radar and a monitoring and identification method therefor are provided. The monitoring radar may be a physiological information monitoring radar. The monitoring and identification method may be a physiological information monitoring and identification method. The physiological information monitoring radar processes at least one reflected radar signal to obtain a response characteristic and range information corresponding to each of a plurality of to-be-monitored objects and distinguishes the response characteristic of each of the to-be-monitored objects as identification information or physiological information. The physiological information monitoring radar then labels each
(Continued)

piece of physiological information according to the range information and the identification information.

26 Claims, 11 Drawing Sheets

(51) Int. Cl.
    *G01S 7/41*     (2006.01)
    *G01S 13/58*     (2006.01)
    *G01S 13/75*     (2006.01)
    *G01S 13/82*     (2006.01)

(52) U.S. Cl.
    CPC .............. *G01S 7/356* (2021.05); *G01S 7/412* (2013.01); *G01S 13/584* (2013.01); *G01S 13/756* (2013.01); *G01S 13/825* (2013.01)

(58) Field of Classification Search
    CPC .... G01S 13/756; G01S 13/825; G01S 13/753; G01S 13/767; G01S 13/876; G01S 13/88; G01S 13/32; G01S 13/36; G01S 7/415; G01S 13/56; G01S 13/58; G01S 13/582; G01S 13/723; G01S 7/417; G06K 7/10009
    See application file for complete search history.

(56) References Cited

U.S. PATENT DOCUMENTS

| | | | |
|---|---|---|---|
| 7,567,200 | B1 | 7/2009 | Osterweil |
| 7,884,753 | B2 | 2/2011 | Peczalski et al. |
| 9,833,200 | B2* | 12/2017 | Lin ..................... H04L 27/2273 |
| 11,169,254 | B2* | 11/2021 | Tsai ....................... G01S 13/723 |
| 2008/0074307 | A1 | 3/2008 | Boric-Lubecke et al. |
| 2010/0231410 | A1 | 9/2010 | Seisenberger et al. |
| 2012/0022348 | A1* | 1/2012 | Droitcour ............ A61B 5/0816 600/407 |
| 2012/0268308 | A1 | 10/2012 | Tuttle et al. |
| 2014/0184447 | A1 | 7/2014 | Zhou et al. |
| 2016/0363648 | A1 | 12/2016 | Mindell et al. |
| 2018/0172813 | A1* | 6/2018 | Rao ........................ G01S 13/343 |
| 2018/0301945 | A1 | 10/2018 | Ishida et al. |
| 2019/0094350 | A1* | 3/2019 | Baheti ..................... G01S 7/415 |
| 2020/0165934 | A1 | 5/2020 | Schleif et al. |
| 2020/0200892 | A1* | 6/2020 | Rajab .................... G01S 13/753 |
| 2020/0237252 | A1 | 7/2020 | Lane et al. |
| 2020/0389770 | A1 | 12/2020 | Marschalkowski et al. |

FOREIGN PATENT DOCUMENTS

| | | |
|---|---|---|
| EP | 0853245 A2 | 7/1998 |
| EP | 3477335 A1 | 5/2019 |
| JP | 3675741 B2 | 7/2005 |
| JP | 2019092726 A | 6/2019 |
| JP | 2020118598 A | 8/2020 |
| WO | 2018/206934 A1 | 11/2018 |
| WO | 2020128150 A1 | 6/2020 |

OTHER PUBLICATIONS

EESR dated Feb. 16, 2022, listed in related European patent application No. 21 190 277.0.
Rao, S.; "Introduction to mmwave Sensing: FMCW Radars;" Texas Instruments; pp. 1-70.
Office Action dated Mar. 7, 2023, listed in related U.S. Appl. No. 17/353,797 (copy not provided).
Office action dated Aug. 4, 2023, listed in related U.S. Appl. No. 17/353,797 (copy not provided).
Office action dated Mar. 22, 2024, listed in related European patent application No. 21 190 299.4.
Strobel, A., et al.; "A Millimeter-Wave Low-Power Active Backscatter Tag for FMCW Radar Systems;" IEEE Transactions on Microwave Theory and Techniques, vol. 61, No. 5, May 2013; pp. 1964-1972.
Lazaro, A., et al.; "Backscatter Transponder Based on Frequency Selective Surface for FMCW Radar Applications;" RadioEngineering, vol. 23, No. 2, Jun. 2014; pp. 632-641.

* cited by examiner

PHYSIOLOGICAL INFORMATION MONITORING AND IDENTIFICATION METHOD, CHARACTERIZATION INFORMATION MONITORING AND IDENTIFICATION METHOD, AND PHYSIOLOGICAL INFORMATION MONITORING RADAR

CROSS-REFERENCES TO RELATED APPLICATIONS

This non-provisional application claims priority under 35 U.S.C. § 119(a) to Patent Application No. 110109639 filed in Taiwan, R.O.C. on Mar. 17, 2021 and Patent Application No. 110109487 filed in Taiwan, R.O.C. on Mar. 17, 2021, the entire contents of which are hereby incorporated by reference.

BACKGROUND

Technical Field

The present invention relates to radar technologies, and in particular, to a characterization information monitoring and identification method by using a reflected radar signal identification and response device and a monitoring radar system applying the method.

Related Art

A radar technology may be applied to various purposes such as distance measurement. However, during measurement of a plurality of objects, an object to which measured information belongs cannot be identified.

SUMMARY

In view of the above, according to some embodiments, a physiological information monitoring and identification method includes: transmitting at least one incident radar signal to a field; receiving at least one reflected radar signal corresponding to the field; processing the reflected radar signal to obtain a response characteristic and range information corresponding to each of a plurality of to-be-monitored objects; distinguishing the response characteristic of each of the plurality of to-be-monitored objects as identification information or physiological information; and labelling each piece of physiological information according to the range information and the identification information.

According to some embodiments, a radar signal processing method for monitoring and identifying characterization information includes: receiving at least one piece of radar digital monitoring data; processing the radar digital monitoring data to obtain a response characteristic and range information corresponding to each of the plurality of to-be-monitored objects; distinguishing the response characteristic of each of the plurality of to-be-monitored objects as identification information or characterization information; and labelling each piece of characterization information according to the range information and the identification information.

According to some embodiments, a physiological information monitoring radar includes a transceiver and a signal processing module. The transceiver is configured to transmit at least one incident radar signal to a field and receive at least one reflected radar signal corresponding to the field. The signal processing module is configured to process the reflected radar signal to obtain a response characteristic and range information corresponding to each of a plurality of to-be-monitored objects, distinguish the response characteristic of each of the plurality of to-be-monitored objects as identification information or physiological information, and label each piece of physiological information according to the range information and the identification information.

According to some embodiments, the range information includes distance information or orientation information.

According to some embodiments, in response to the response characteristic being the identification information, it is determined that the to-be-monitored object associated with the identification information is a response device.

According to some embodiments, the identification information is a vibration frequency of the response device or a change in a radar cross section of the response device.

According to some embodiments, in response to the response characteristic being the physiological information, it is determined that the to-be-monitored object associated with the physiological information is a living body, and the response characteristic is identified as the physiological information of the living body. According to some embodiments, in response to the response characteristic being speed information, it is determined that the to-be-monitored object associated with the speed information is a moving object, and the response characteristic is identified as the speed information of the moving body.

According to some embodiments, the step of labelling each piece of physiological information according to the range information and the identification information includes: in response to the range information of a specific living body matching the range information of a specific response device, labelling the physiological information of the specific living body by using the identification information of the specific response device.

According to some embodiments, the physiological information monitoring radar is a frequency modulated continuous wave radar, and the incident radar signal is a frequency modulated radar signal.

In conclusion, according to the physiological information monitoring radar and the physiological information monitoring and identification method in some embodiments, physiological information of a subject may be measured, and the physiological information is labelled through identification information of an identification and response device of the radar, so as to learn an identity of the subject.

DETAILED DESCRIPTION

The term "connect" used herein means that two or more elements are directly in physical or electrical contact with each other or are indirectly in physical or electrical contact with each other.

Figure 1:
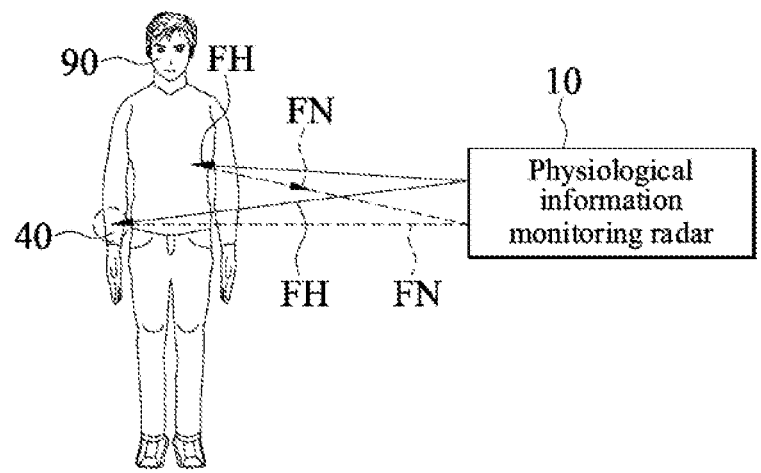
FIG. 1 is a schematic diagram of a use state of a radar system according to some embodiments.

FIG. 1 is a schematic diagram of a use state of a radar system according to some embodiments. The radar system includes a physiological information monitoring radar 10 and at least one response device 40. One response device 40 is exemplified herein. The response device 40 may be disposed at a specified point (such as a resting position of a subject 90) or carried on the subject 90. The physiological information monitoring radar 10 transmits a radar signal (which is referred to as an "incident radar signal FH" below). The incident radar signal FH transmitted to a to-be-monitored object is modulated under a movement of the to-be-monitored object (such as the subject 90 and the response device 40) and is reflected back to the physiological information monitoring radar 10. The reflected radar signal is referred to as a "reflected radar signal FN" below. Therefore, one or more types of information of the to-be-monitored object may be monitored by analyzing the reflected radar signal FN. The information may be, for example, a speed, a distance, an orientation, a movement in a small range (such as a vibration frequency, physiological information (such as a heartbeat or a breath)), etc.

In some embodiments, the physiological information monitoring radar 10 may be a frequency modulated continuous wave (FMCW) radar, a continuous wave (CW) radar, or an ultra-wideband (UWB) radar. The frequency modulated continuous wave radar is exemplified below for description.

Figure 2:
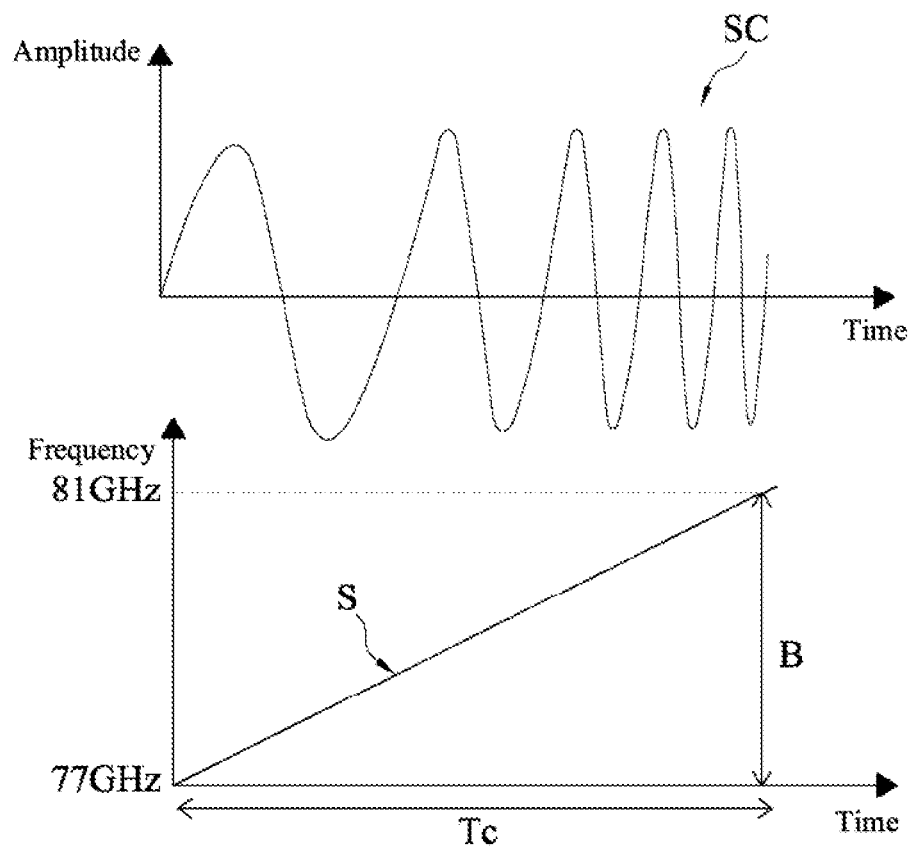
FIG. 2 is a schematic diagram illustrating a radar signal.

Referring to FIG. 2, FIG. 2 is a schematic diagram illustrating a radar signal. An upper half presents a change of an amplitude of the incident radar signal FH over time, and a lower half presents a change of a frequency of the incident radar signal FH over time. The incident radar signal FH includes a plurality of chirp pulses SC. For clarity of the diagram, FIG. 2 presents only one chirp pulse SC. The chirp pulse SC is a linear frequency modulated pulse signal herein, which is a sine wave whose frequency increases linearly over time. In some embodiments, the frequency of the chirp pulse SC increases non-linearly. For ease of description, a linear way is exemplified below for description. As shown in FIG. 2, within a duration Tc (for example, 40 microseconds), the chirp pulse SC linearly increases from a start frequency (for example, 77 GHz) to a stop frequency (for example, 81 GHz) according to a slope S. The start frequency and the stop frequency may be selected from the millimeter wave band (that is, 30 GHz to 300 GHz). A difference between the start frequency and the stop frequency is a pulse bandwidth B.

Figure 3:
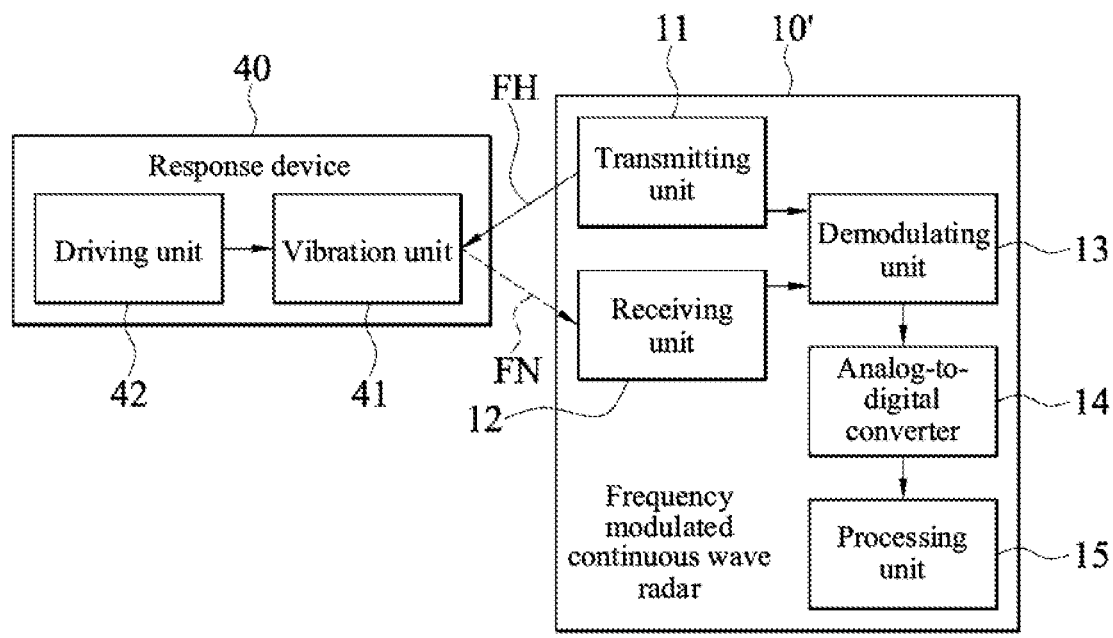
FIG. 3 is a schematic block diagram of a radar system according to some embodiments.

FIG. 3 is a schematic block diagram of a radar system according to some embodiments. In some embodiments, the response device 40 includes a vibration unit 41 and a driving unit 42. The vibration unit 41 has a reflecting surface serving as a radar cross section (RCS). The driving unit 42 drives the vibration unit 41 to vibrate at a vibration frequency, so that the incident radar signal FH is modulated under a movement of the reflecting surface. In other embodiments, the response device 40 includes a backscatter transponder. The incident radar signal FH is reflected through the reflecting surface. A frequency modulated continuous wave radar 10' receives the reflected radar signal FN and demodulates the reflected radar signal FN to obtain a vibration frequency, a modulation frequency, or a change in a radar cross section of the response device 40. Therefore, for response devices 40 having different vibration frequencies, modulation frequencies, or changes in a radar cross section, the frequency modulated continuous wave radar 10' may identify a specific response device 40 by using the different vibration frequencies, modulation frequencies, or changes in the radar cross section as identification information. Approximate response devices 40 and subjects 90 can be determined through comparison by using distance information and orientation information (which are collectively referred to as range information), and a subject 90 to which monitored physiological information or speed information (which is collectively referred to characterization information) belongs can be determined. How to calculate the information is described below.

Figure 4:
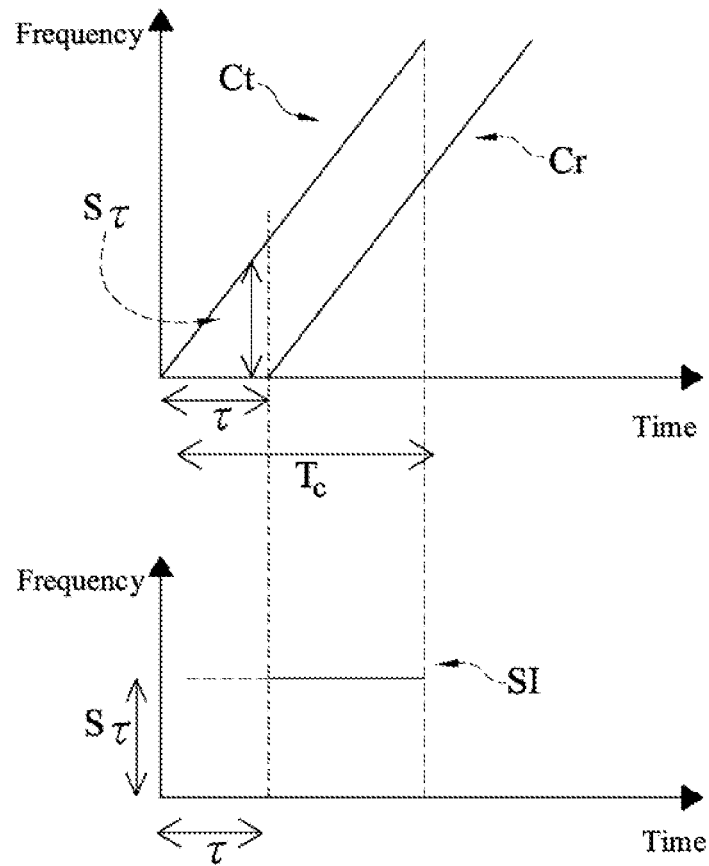
FIG. 4 is a schematic diagram illustrating an incident radar signal and a reflected radar signal.

Refer to FIG. 3 and FIG. 4 together. FIG. 4 is a schematic diagram illustrating an incident radar signal FH and a reflected radar signal FN. The frequency modulated continuous wave radar 10' includes a transmitting unit 11, a receiving unit 12, a demodulating unit 13, an analog-to-digital converter 14, and a processing unit 15. The transmitting unit 11 is configured to transmit an incident radar signal FH, and includes a transmitting antenna and a signal synthesizer. The signal synthesizer is configured to generate an incident radar signal FH including a chirp pulse Ct, and transmit the incident radar signal through the transmitting antenna. The receiving unit 12 includes a receiving antenna configured to receive a reflected radar signal FN including a chirp pulse Cr. The chirp pulse Cr may be considered as a delayed chirp pulse Ct. The demodulating unit 13 is connected to the transmitting unit 11 and the receiving unit 12, and includes a mixer and a low-pass filter. The mixer couples the chirp pulse Ct of the incident radar signal FH with the chirp pulse Cr of the reflected radar signal FN to generate two coupled signals which are respectively a sum of frequencies of the two chirp pulses Ct and Cr and a difference between the frequencies. The low-pass filter performs low-pass filtering on the coupled signal to remove high-frequency components, to obtain a coupled signal which is the difference between the frequencies of the two chirp pulses Ct and Cr, which is referred to as an "intermediate frequency signal SI" below. The analog-to-digital converter 14 converts the intermediate frequency signal SI to a digital signal. The processing unit 15 performs digital signal processing on the digital signal. The processing unit 15 may be, for example, a central processing unit (CPU), a graphics processing unit (GPU), or other programmable general-purpose or special-purpose microprocessors, a digital signal processor (DSP), a programmable controller, an application specific integrated circuit (ASIC), a programmable logic device (PLD), or other similar devices, chips, integrated circuits, and a combination thereof.

Referring to FIG. 4, a frequency $f_0$ of the intermediate frequency signal SI may be expressed as equation 1. S is a slope, and τ is a delay time between transmission of the incident radar signal FH and reception of the reflected radar signal FN. Therefore, τ may be expressed as equation 2. d is a distance between a radar transmitting antenna and the to-be-monitored object, and c is the speed of light. Equation 3 may be obtained by substituting equation 2 into equation 1. It can be learned from equation 3 that the frequency $f_0$ of the intermediate frequency signal SI implicitly contains distance information (that is, a distance between the frequency modulated continuous wave radar 10' and the to-be-monitored object).

$$f_0 = S \cdot \tau \quad \text{Equation 1}$$

$$\tau = 2d/c \quad \text{Equation 2}$$

$$f_0 = 2Sd/c \quad \text{Equation 3}$$

Figure 5:
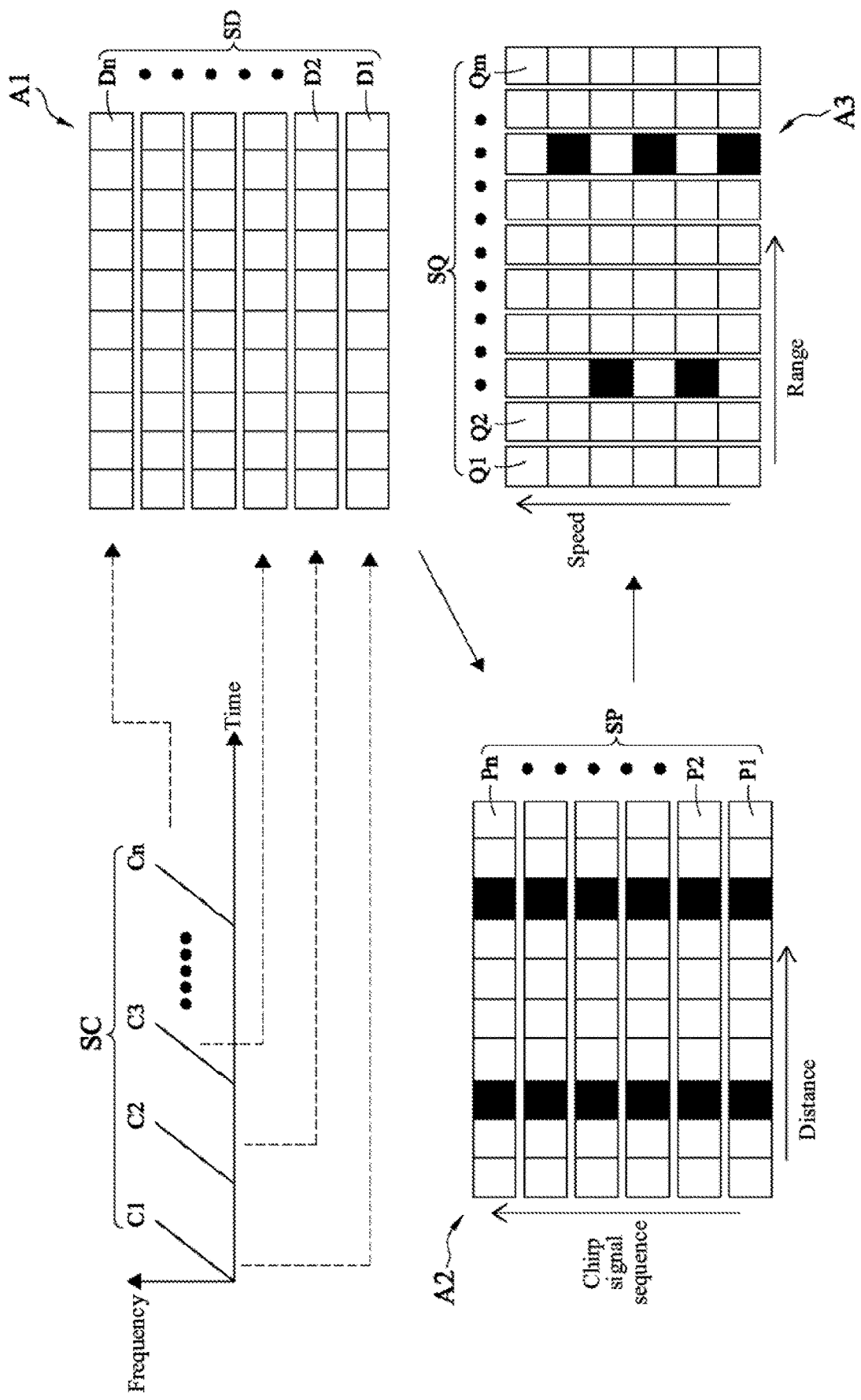
FIG. 5 is a schematic diagram of signal processing according to some embodiments.

FIG. 5 is a schematic diagram of signal processing according to some embodiments. Chirp pulses SC are sequentially numbered as C1, C2, C3, . . . , Cn herein, where n is a positive integer. The analog-to-digital converter 14 converts received intermediate frequency signals SI corresponding to the chirp pulses C1 to Cn to digital signals SD (which are respectively expressed as D1, D2, . . . , Dn, where n is a positive integer). A value of each of the digital signals SD may be expressed as a one-dimensional array (a row matrix). The row matrices are arranged longitudinally in sequence to form a two-dimensional array A1. It may be understood that the digital signals SD may also be arranged into column matrices and arranged horizontally in sequence to form a two-dimensional array. A value of the two-dimensional array A1 represents a signal strength (an amplitude). Index values of the columns of the two-dimensional array A1 correspond to the sequence of the chirp pulses SC (the digital signals SD). An index value of the row of the two-dimensional array A1 has a time implication, that is, the row matrix of the two-dimensional array A1 is a time-domain signal.

The processing unit 15 performs Fast Fourier transform (FFT) (which is referred to as "range Fast Fourier transform, range FFT" below) on each of the row matrices of the two-dimensional array A1 (that is, the digital signal SD) to obtain frequency-domain signals SP (which are respectively expressed as P1, P2, . . . , Pn, where n is a positive integer), that is, the two-dimensional array A2. Therefore, the row matrices of the two-dimensional array A2 are equivalent to spectral distribution. As described above, the frequency of the intermediate frequency signal SI implicitly contains the distance information. In other words, the index value of the row of the two-dimensional array A2 has a distance implication. The values of the two-dimensional array A2 represent strengths of frequencies on a spectrum, which can present strengths of radar signals reflected at different distances from the frequency modulated continuous wave radar 10'. As shown in FIG. 5, a colored box in the two-dimensional array A2 is a peak value (that is, a value exceeding a threshold), indicating that there is a to-be-monitored object at a distance corresponding to the frequency. The distance between the frequency modulated continuous wave radar 10' and the to-be-monitored object may be calculated based on the peak frequency. Further, movement information (such as an average speed) within a wide range may be calculated according to calculated distance changes of a specific to-be-monitored object at different time points.

A time interval between the chirp pulses SC is very short (for example, tens of microseconds). Relatively speaking, a position of the same to-be-monitored object that reflects the chirp pulses SC is substantially unchanged. Therefore, each frequency-domain signal SP has a colored box corresponding to the same distance, presenting a column of colored boxes. As shown in FIG. 5, two columns of colored boxes are exemplified herein. Since the frequency-domain signals SP has a peak in the same column, a slight movement change cannot be embodied in the frequency, However, a phase component is significantly affected. The index values of the columns of the two-dimensional array A2 correspond to the sequence of the frequency-domain signals SP (the chirp pulses SC), which mean a time sequence. Therefore, each column matrix of the two-dimensional array A2 may be considered as a time-domain signal. The processing unit 15 performs Fast Fourier transform (which is referred to as "Doppler Fast Fourier transform, Doppler FFT" below) on each column matrix of the two-dimensional array A2 to obtain phase frequency-domain signals SQ (which are respectively expressed as Q1, Q2, . . . , Qm, where m is a positive integer), that is, a two-dimensional array A3. Therefore, the column matrices of the two-dimensional array A3 are equivalent to phase spectrum distribution. A phase $\phi_0$ of the intermediate frequency signal SI may be expressed as equation 4. By substituting equation 2 into equation 4, equation 5 can be obtained. λ is a wavelength. According to equation 5, equation 6 can be derived. v is a speed, Δϕ is a phase difference between two adjacent chirp pulses (Cn−1 and Cn), and Δt is a time difference between two adjacent chirp pulses SC. It can be learned from equation 6 that a phase of the intermediate frequency signal SI implicitly contains movement information (a speed). Therefore, an index value of the column of the two-dimensional array A3 has a speed implication. A moving speed or a cyclic movement frequency of the to-be-monitored object may be calculated based on the phase frequency-domain signal SQ, so that movement information (such as speed information) and physiological information (such as a breathing rate and a heartbeat frequency) of the subject 90 and the vibration frequency, the modulation frequency, or the change in the radar cross section of the response device 40 can be obtained. In the two-dimensional array A3 shown in FIG. 5, two columns respectively have two colored boxes (peak values exceeding a threshold) and three colored boxes (peak values exceeding a threshold), indicating that there are at least two to-be-monitored objects at two different distances from the frequency modulated continuous wave radar 10'. A speed (a frequency) corresponding to each of the colored boxes is small-range movement information (such as a speed), physiological information, a vibration frequency, a modulation frequency, or a change in a radar cross section corresponding to at least one of the to-be-monitored objects.

$$\phi_0 = 2\pi f_0 \tau \quad \text{Equation 4}$$

$$\phi_0 = \frac{4\pi d}{\lambda} \quad \text{Equation 5}$$

$$v = \frac{\lambda \Delta \phi}{4\pi \Delta t} \quad \text{Equation 6}$$

In some embodiments, the processing unit 15 may not perform the Fast Fourier transform on the entire two-dimensional array A2, but perform the Fast Fourier transform on only the same peak values of the frequency-domain signals SP (which are two column matrices represented by colored boxes), to reduce an amount of calculation and a calculation time.

It may be understood from the above description that, after the intermediate frequency signal SI undergoes analog-to-digital conversion, the processing unit 15 performs digital signal processing on the intermediate frequency signal, so that the movement information and the physiological information (such as the breathing rate and the heartbeat frequency) of the subject 90 and the vibration frequency, the modulation frequency, or the change in the radar cross section of the response device 40 can be obtained.

In the above description, the transmitting unit 11 is exemplified as having one transmitting antenna and the receiving unit 12 as having one receiving antenna. However, in some embodiments, the transmitting unit 11 has a plurality of transmitting antennas for transmit a plurality of incident radar signals FH. The receiving unit 12 has one receiving antenna, and the receiving antenna receives a plurality of reflected radar signals FN corresponding to the incident radar signals FH. The reflected radar signals FN are demodulated into a plurality of intermediate frequency signals SI by the demodulating unit 13. The analog-to-digital converter 14 converts the intermediate frequency signals SI to digital signals. The processing unit 15 performs digital signal processing on the digital signals, and obtains a direction (orientation information) of the to-be-monitored object (such as the subject 90 or the response device 40) by using an angle of departure (AOD) direction-finding function. However, the present disclosure is not limited thereto. In some other embodiments, the frequency modulated continuous wave radar 10' obtains the direction (the orientation information) of the to-be-monitored object (such as the subject 90 or the response device 40) through a multiple signal classification (MUSIC) algorithm. In other embodiments, the frequency modulated continuous wave radar 10' obtains the direction (the orientation information) of the to-be-monitored object (such as the subject 90 or the response device 40) through a Capon algorithm.

In some embodiments, the transmitting unit 11 has one transmitting antenna for transmitting one incident radar signal FH. The receiving unit 12 has a plurality of receiving antennas for receiving reflected radar signals FN. The reflected radar signals FN are demodulated into a plurality of intermediate frequency signals SI by the demodulating unit 13. The analog-to-digital converter 14 converts the intermediate frequency signals SI to digital signals. The processing unit 15 performs digital signal processing on the digital signals, and obtains a direction (orientation information) of the to-be-monitored object (such as the subject 90 or the response device 40) by using an angle of arrival (AOA) direction-finding function.

Figure 6:
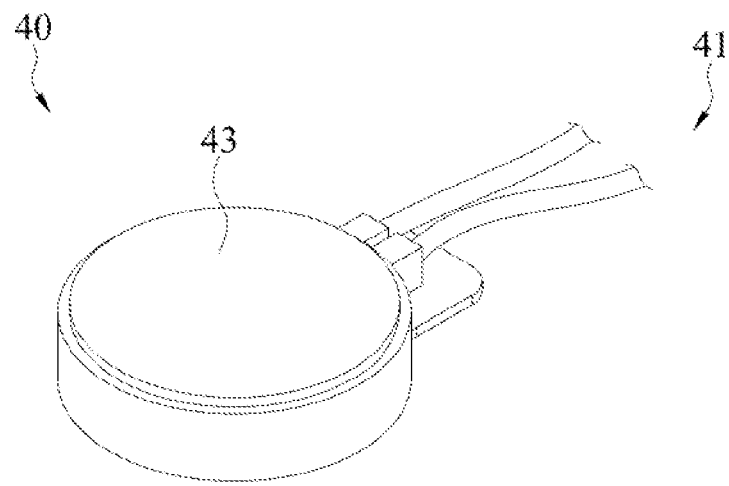
FIG. 6 is a perspective view of a first variation of a response device according to some embodiments.

FIG. 6 is a partial perspective view of a first variation of the response device according to some embodiments. In the embodiments, the response device 40 includes a vibration unit 41. The vibration unit 41 may be a vibrator, and an upper surface thereof serves as a reflecting surface 43. The response device 40 further includes a driving unit 42. The driving unit 42 has a driving circuit and is connected to the vibration unit 41 for controlling the vibrator to vibrate at a vibration frequency.

Figure 7:
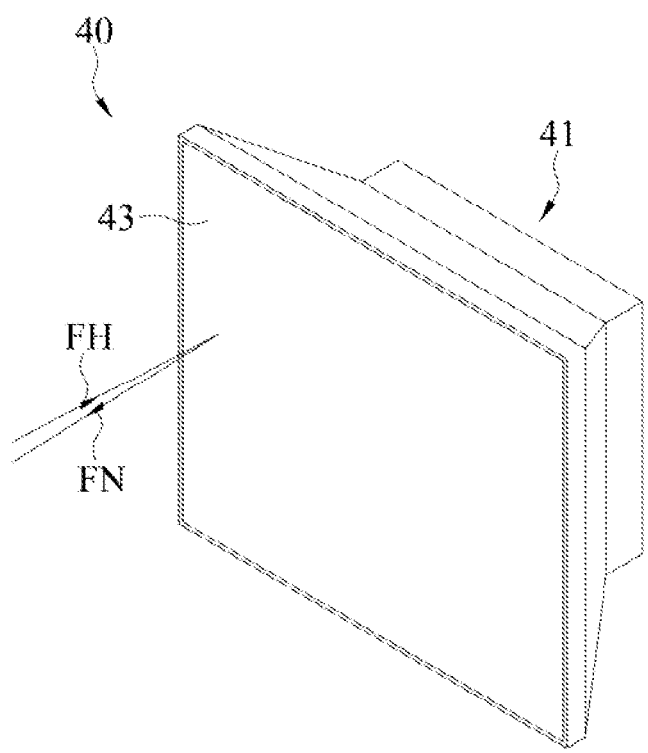
FIG. 7 is a perspective view of a second variation of the response device according to some embodiments.

FIG. 7 is a perspective view of a second variation of the response device according to some embodiments. In the embodiments, the response device 40 includes a vibration unit 41. The vibration unit 41 may be a speaker driver, such as a moving-coil speaker driver or a flat panel speaker driver. As shown in FIG. 3, the response device 40 further includes a driving unit 42. In these embodiments, the driving unit 42 has an oscillation control circuit for driving the speaker driver and controlling a vibration frequency of a diaphragm of the speaker driver. The diaphragm serves as the reflecting surface 43 herein, and the reflecting surface 43 may have a metal reflecting layer to enhance a reflection effect.

Figure 8:
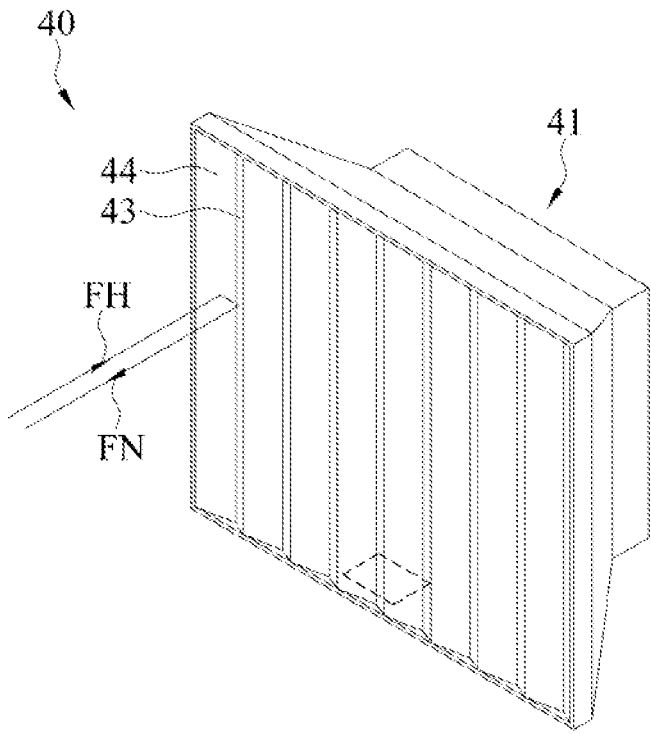
FIG. 8 is a perspective view of a third variation of the response device according to some embodiments.

FIG. 8 is a perspective view of a third variation of the response device according to some embodiments. In the embodiments, the response device 40 includes a vibration unit 41. A difference from FIG. 7 is that the diaphragm (that is, the reflecting surface 43) includes a plurality of corner reflectors 44 arranged adjacent to each other. Each of the corner reflectors 44 is a dihedral corner reflector herein, which is composed of two surfaces perpendicular to each other. In this way, the incident radar signal FH and the reflected radar signal FN can be parallel to each other, and the reflection effect can be enhanced, helping the frequency modulated continuous wave radar 10' receive the reflected radar signal FN.

Figure 9:
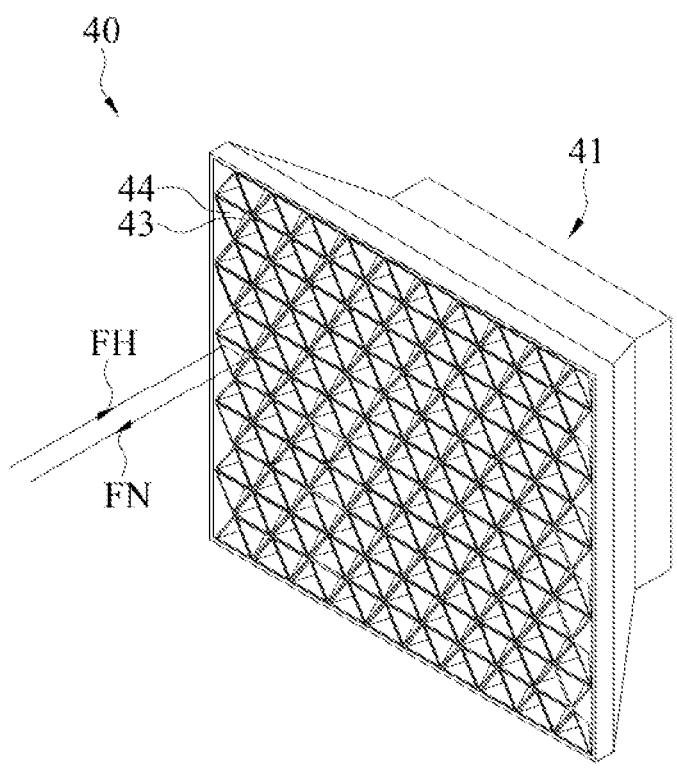
FIG. 9 is a perspective view of a fourth variation of the response device according to some embodiments.

FIG. 9 is a perspective view of a fourth variation of the response device according to some embodiments. In the embodiments, the response device 40 includes a vibration unit 41. A difference from FIG. 8 is that the corner reflector 44 is a trihedral corner reflector, which is composed of three surfaces perpendicular to each other. Similarly, the incident radar signal FH and the reflected radar signal FN can be parallel to each other, and the reflection effect can be enhanced, helping the frequency modulated continuous wave radar 10' receive the reflected radar signal FN.

Figure 10:
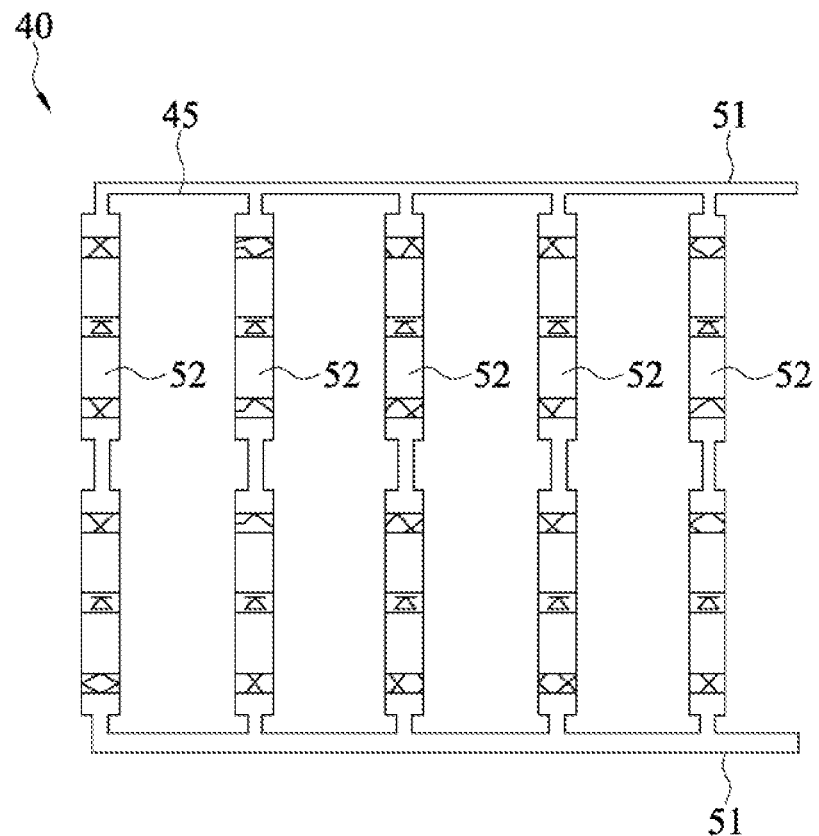
FIG. 10 is a schematic diagram of a fifth variation of the response device according to some embodiments.

FIG. 10 is a schematic diagram of a fifth variation of the response device 40 according to some embodiments. In the embodiments, the response device 40 includes a backscatter transponder 45. The backscatter transponder 45 includes two main lines 51 and a plurality of branch lines 52 side by side. The main line 51 is configured to receive a bias voltage. The branch lines 52 are connected between the two main lines. The branch lines 52 each are provided with a phase shift switch diode (PIN diode) and a matching resistor. Biasing of the phase shift switch diode may cause the formation of a frequency selective surface (FSS) for frequency modulation. A backscatter response to the incident radar signal FH may be modulated by using a radar cross section (RCS) of the frequency selective surface. Therefore, the reflected radar signal FN will have a modulation frequency of the backscatter transponder 45. In this way, the frequency modulated continuous wave radar 10' can obtain the modulation frequency (the change in the radar cross section) of the backscatter transponder 45 through the above signal processing, so as to identify the response device 40.

Figure 11:
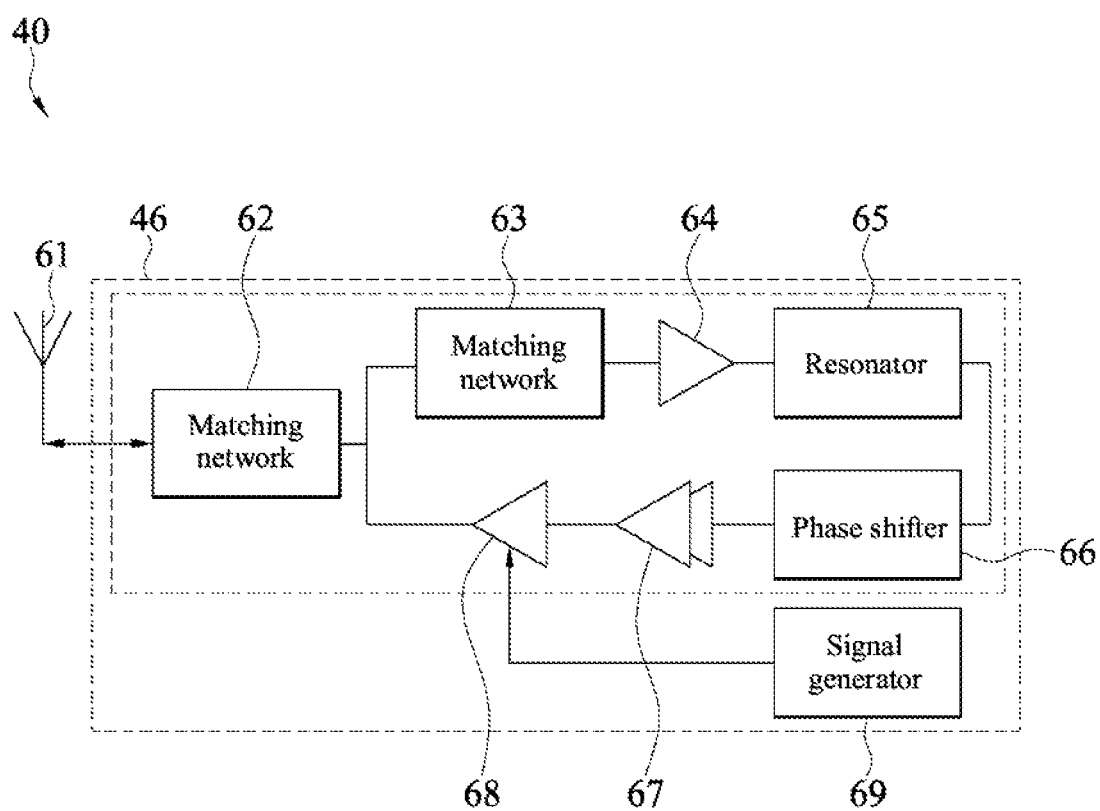
FIG. 11 is a schematic block diagram of a sixth variation of the response device according to some embodiments.

FIG. 11 is a schematic block diagram of a sixth variation of the response device 40 according to some embodiments. In the embodiments, the response device 40 includes an active backscatter transponder 46 for modulating the incident radar signal FH according to a modulation frequency. The active backscatter transponder 46 includes an antenna 61, matching networks 62 and 63, a low noise amplifier 64, a resonator 65, a phase shifter 66, a power amplifier driver 67, a power amplifier 68, and a signal generator 69. The antenna 61 receives the incident radar signal FH. The matching networks 62 and 63 are used for impedance matching. The incident radar signal FH is processed by the low noise amplifier 64 to resonate with the resonator 65, and is then amplified through the power amplifier driver 67 and the power amplifier 68 after phase compensation by the phase shifter 66. The signal generator 69 generates a control signal for switching the power amplifier 68 at a modulation frequency, so as to transmit the signal amplified by the power amplifier 68 through the antenna 61. Therefore, the reflected radar signal FN will have the modulation frequency of the backscatter transponder 45. In this way, the frequency modulated continuous wave radar 10' can obtain the modulation frequency (the change in the radar cross section) of the backscatter transponder 45 through the above signal processing, so as to identify the response device 40. More specifically, the frequency modulated continuous wave radar 10' may first find two distance frequencies corresponding to the modulation frequency (an identity frequency) of the active backscatter transponder 46 after performing signal processing (range FFT), and then add up and average the two distance frequencies to obtain an actual distance frequency, and subtract and average the two distance frequencies to obtain the modulation frequency (the identity frequency).

In the above description, the vibration frequency, the modulation frequency, or the change in the radar cross section of the response device 40 is exemplified as a single frequency. As shown in Table 1, the vibration frequency, the modulation frequency, or the change in the radar cross section of each response device 40 in any time period remains constant. However, in some embodiments, the vibration frequency, the modulation frequency, or the change in the radar cross section of the response device 40 is a time-varying frequency. In other words, the vibration frequency, the modulation frequency, or the change in the radar cross section of the response device is changed in different time periods. As shown in Table 2, each response device 40 has a different frequency combination. In this way, digital encoding achieved by using frequency changes can be formed. By setting different codes for different response devices 40, the frequency modulated continuous wave radar 10' can identify the response devices 40. Table 3 presents another encoding manner. No-response (for example, stop oscillating) (marked as NA) within some time periods may also be used as a coding form. Table 4 presents still another encoding manner. The vibration frequency, the modulation frequency, or the change in the radar cross section may be set to a fixed single frequency, and different response devices 40 are set to respond in different time period combinations.

TABLE 1

|  | First time period | Second time period | Third time period | Fourth time period | Fifth time period |
| --- | --- | --- | --- | --- | --- |
| Response device A | F1 | F1 | F1 | F1 | F1 |
| Response device B | F2 | F2 | F2 | F2 | F2 |
| Response device C | F3 | F3 | F3 | F3 | F3 |

TABLE 2

|  | First time period | Second time period | Third time period | Fourth time period | Fifth time period |
| --- | --- | --- | --- | --- | --- |
| Response device A | F1 | F2 | F1 | F1 | F3 |
| Response device B | F2 | F3 | F2 | F2 | F3 |
| Response device C | F3 | F2 | F1 | F1 | F1 |

TABLE 3

|  | First time period | Second time period | Third time period | Fourth time period | Fifth time period |
| --- | --- | --- | --- | --- | --- |
| Response device A | F1 | F2 | NA | F1 | F3 |
| Response device B | F2 | F3 | NA | F3 | NA |
| Response device C | F3 | NA | F2 | F1 | F3 |

TABLE 4

|  | First time period | Second time period | Third time period | Fourth time period | Fifth time period |
| --- | --- | --- | --- | --- | --- |
| Response device A | F1 | NA | NA | F1 | NA |
| Response device B | F1 | F1 | NA | F1 | F1 |
| Response device C | F1 | NA | F1 | NA | NA |

Figure 12:
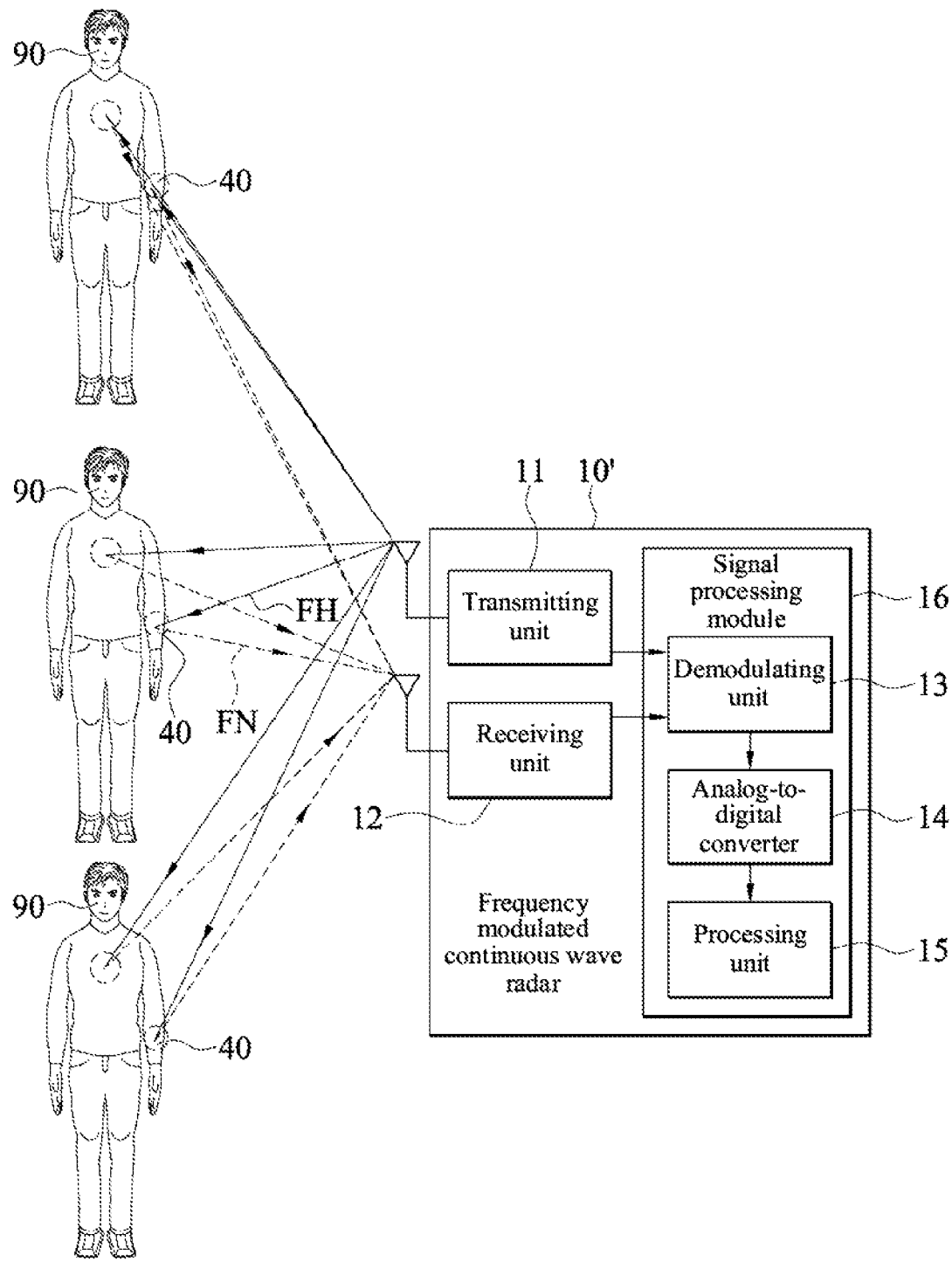
FIG. 12 is a schematic diagram of a use state of a radar system according to some embodiments.

FIG. 12 is a schematic diagram of a use state of a radar system according to some embodiments. Elements and signals with similar functions are represented by using the same symbol herein for simplicity, and the above demodulating unit 13, analog-to-digital converter 14, and processing unit 15 are collectively referred to as a signal processing module 16, and the transmitting unit 11 and the receiving unit 12 are collectively referred to as a transceiver.

In another embodiment of the present disclosure, the frequency modulated continuous wave radar 10' further includes a transmitting module connected to the signal processing module 16. The transmitting module is configured to transmit a result obtained through digital signal processing by the signal processing module 16 to an edge device or a cloud server at the other end.

In another embodiment of the present disclosure, the signal processing module 16 of the frequency modulated continuous wave radar 10' only processes some of the digital signals SD from the analog-to-digital converter 14, and processing results of some of the digital signals are transmitted to the edge device or the cloud server at the other end through a transmitting module of the frequency modulated continuous wave radar 10' for subsequent digital signal processing and calculation.

In another embodiment of the present disclosure, the signal processing module 16 of the frequency modulated continuous wave radar 10' does not process the digital signals SD from the analog-to-digital converter 14. Instead, the digital signals SD from the analog-to-digital converter 14 are transmitted to the edge device or the cloud server at the other end through a transmitting module of the frequency modulated continuous wave radar 10' for digital signal processing and calculation.

Figure 13:
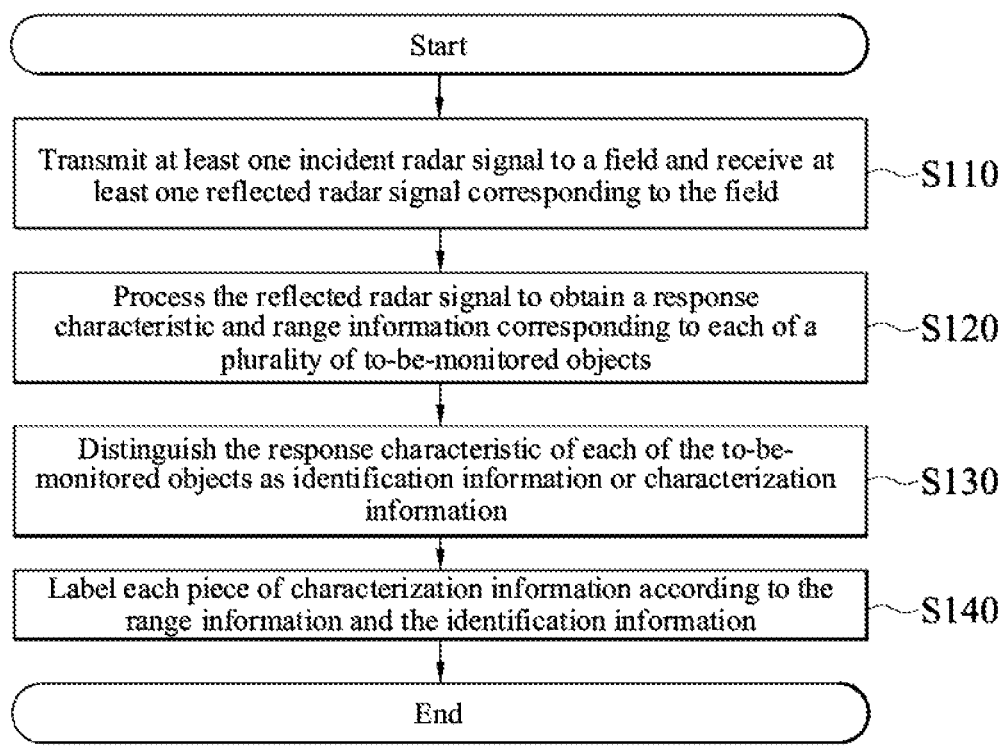
FIG. 13 is a flowchart of a radar signal processing method according to some embodiments.

Refer to FIG. 12 and FIG. 13 together. FIG. 13 is a flowchart of a radar signal processing method for monitoring and identifying characterization information of the plurality of to-be-monitored objects according to some embodiments. In step S110, the transmitting unit 11 transmits at least one incident radar signal FH to a field, and the above receiving unit receives at least one reflected radar signal FN corresponding to the field. The field has the above to-be-monitored object (that is, one or more subjects 90 and respective response devices 40). In step S120, the signal processing module 16 processes the reflected radar signals FN to obtain a response characteristic corresponding to each of the plurality of to-be-monitored objects (that is, the above physiological information of the subject 90 or the above vibration frequency, modulation frequency, or change in a radar cross section of the response device 40) and range information (that is, the above distance information and/or the orientation information). In other embodiments, if the to-be-monitored subject is the above subject 90, the above subject 90 may further correspond to a plurality of response characteristics (for example, a plurality of pieces of characterization information of the same subject 90, such as breathing information, heartbeat information, and speed information).

In some embodiments, the signal processing module 16 converts the reflected radar signals FN (the chirp pulses C1 to Cn) to a plurality of intermediate frequency signals SI, converts the intermediate frequency signals SI corresponding to the chirp pulses C1 to Cn to a plurality of digital signals SD, performs range FFT on the digital signals SD, and finds a specific frequency (a peak frequency) exceeding a set strength from a frequency domain obtained through the range FFT. The signal processing module 16 then calculates range of the to-be-monitored object (such as the subject 90 or the response device 40) based on a time difference between chirps corresponding to specific frequencies. The signal processing module 16 then performs Doppler FFT on data of specific frequencies that exceed the set strength, and calculates at least one peak value of a corresponding phase frequency. The at least one peak value is a corresponding vibration characteristic of the to-be-monitored object (including a breath and a heartbeat, the vibration frequency, the modulation frequency, or the radar cross section of the response device, or a movement mode of the to-be-monitored object, etc.). In some embodiments, the signal processing module 16 performs digital signal processing on the digital signals, and obtains a direction (orientation information) of the to-be-monitored object (such as the subject 90 or the response device 40) by using an angle of arrival (AOA) direction-finding function.

In step S130, the signal processing module 16 may distinguish the response characteristic of each of the plurality of to-be-monitored objects as identification information or physiological information according to a frequency value. For example, the breathing rate is generally 12-20 times per minute, and the heartbeat frequency is generally 60-100 times per minute. The vibration frequency, the modulation frequency, or the change in the radar cross section of the response device 40 may be set to a frequency value (for example, a frequency value of a plurality of orders of magnitudes) completely different from the breathing rate and the heartbeat frequency. In step S140, the signal processing module 16 labels each piece of physiological information according to the range information and the identification information. In this way, a subject 90 to which the obtained physiological information corresponds can be learned according to the label. In this embodiment, the response device 40 is disposed on the subject 90.

In some embodiments, the signal processing module 16 distinguishes the response characteristic of each of the plurality of to-be-monitored objects as identification information or characterization information (such as physiological information and speed information). The signal processing module 16 labels each piece of characterization information according to the range information and the identification information. In this way, a subject 90 to which the obtained physiological information corresponds can be learned and a moving object to which the obtained speed information corresponds can be learned according to the label. The moving object may be an object or a living body that is moving.

In some embodiments, the response device 40 is disposed adjacent to the subject 90, including but not limited to, at a specific sickbed in a multi-person room, a specific position in the field, or a specific orientation in the field. In some embodiments, the response device 40 serves as a group tag for labelling a plurality of to-be-monitored objects corresponding to the same range information. The range information may be distance information and/or orientation information.

Figure 14:
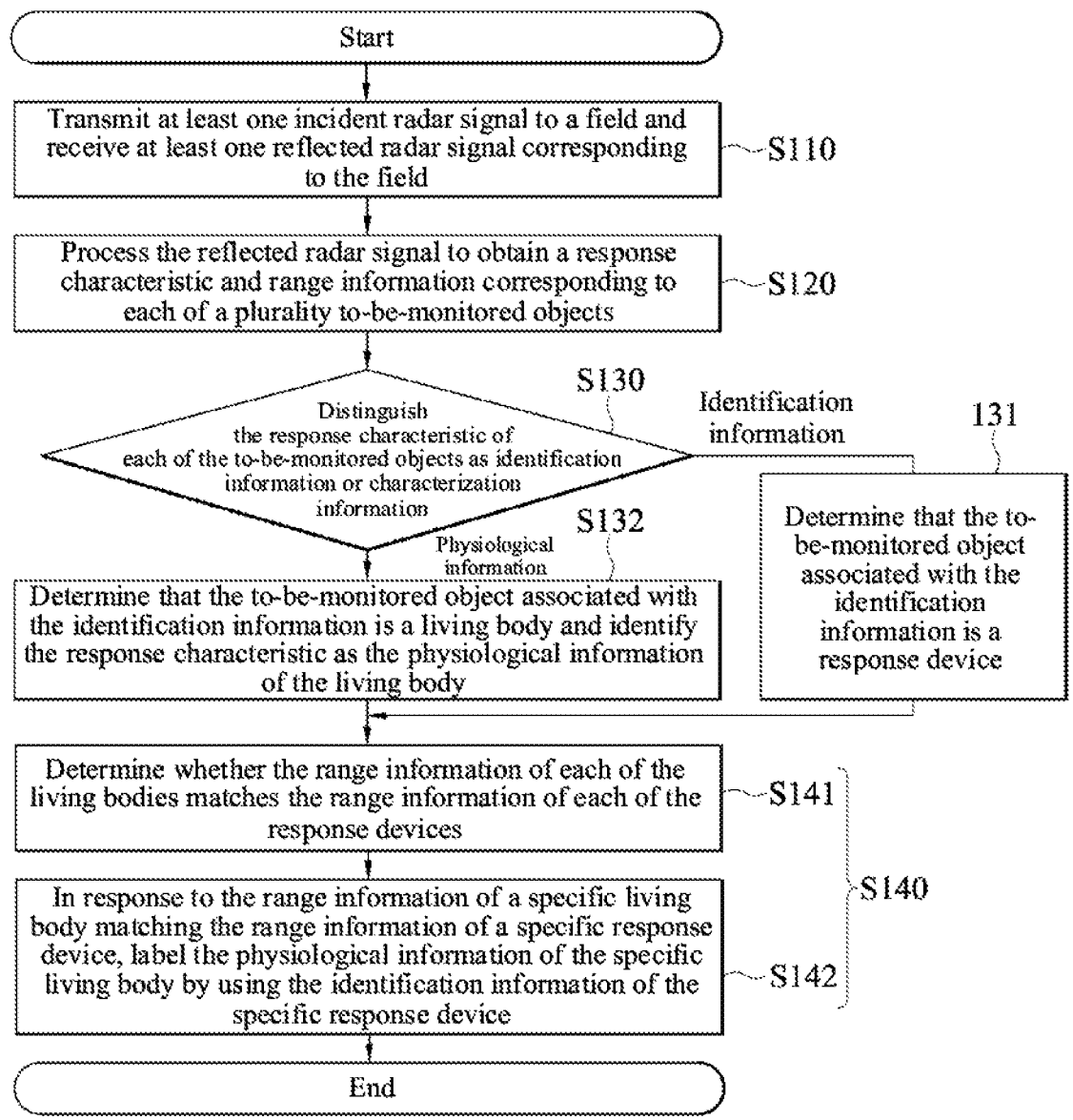
FIG. 14 is a detailed flowchart of a physiological information monitoring and identification method according to some embodiments.

FIG. 14 is a detailed flowchart of a physiological information monitoring and identification method according to some embodiments. After the above step S130, if the response characteristic is the identification information, the signal processing module 16 determines that the to-be-monitored object associated with the identification information is a response device 40 (step S131). If the response characteristic is the physiological information, the signal processing module 16 determines that the to-be-monitored object associated with the identification information is a living body (that is, the above subject 90), and identifies the response characteristic as the physiological information of the living body (step S132).

The above step S140 includes step S141 and step S142. In step S141, the signal processing module 16 determines whether the range information of each of the living bodies (a subject 90) matches the range information of each of the response devices 40. In other words, it is determined whether the subject 90 and the response device 40 are adjacent according to the range information of the subject 90 and the range information of the response device 40. If they are adjacent, it is determined that the two pieces of range information match each other.

In step S142, in response to the range information of the specific living body (the subject 90) matching the range information of the specific response device 40, physiological information of the specific living body (the subject 90) is labelled by using identification information of the specific response device 40. In other embodiments, similarly, the above physiological information monitoring and identification method may be further applied to monitoring and identification of the characterization information (such as speed information) of a specific to-be-monitored object (which may be, but is not limited to, the subject 90). Specifically, a moving speed of a moving object or a moving living body is monitored and identified.

Figure 15:
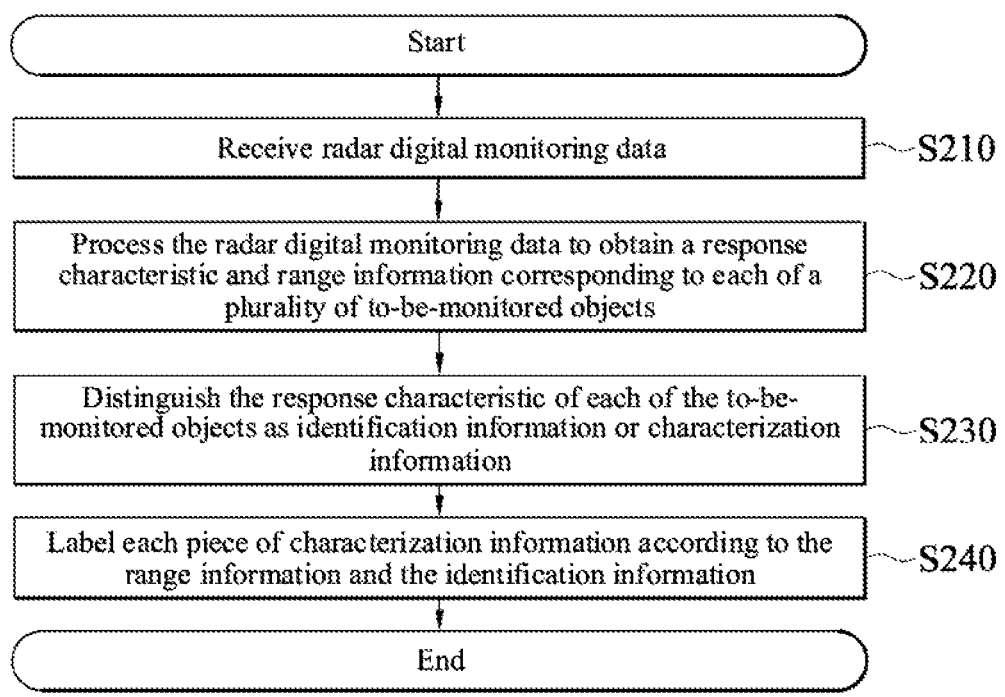
FIG. 15 is another flowchart of the radar signal processing method according to some embodiments.

FIG. 15 is another flowchart of the radar signal processing method according to some embodiments, which may be performed by the above radar system or by an edge device or a cloud server. In other words, after being converted to a digital signal SD (or referred to as radar digital monitoring data) by the signal processing module 16, the above reflected radar signal FN continues to be processed by the signal processing module 16 or is transmitted to the edge device or the cloud server for processing. In step S210, the radar digital monitoring data is received. Step S220 to step S240 are processing performed according to the received radar digital monitoring data, and the processing steps are the same as the above step S120 to step S140. Details are not repeated herein. It may be understood that, as shown in FIG. 14, the method may specifically further include steps S131, S132, S141, and S142.

In conclusion, according to the radar system in some embodiments, the physiological information of the subject 90 may be measured, and the physiological information is labelled through identification information of an identification and response device 40 of the radar, so as to learn an identity of the subject 90.

What is claimed is:

1. A physiological information monitoring and identification method, comprising:
   transmitting a plurality of incident radar signals to a plurality of to-be-monitored objects of a field, wherein the to-be-monitored objects includes at least one response device and at least one living body;
   receiving a first reflected radar signal corresponding to each of the response devices of the field and a second reflected radar signal corresponding to each of the living bodies of the field;
   processing each of the first reflected radar signals, by performing a Doppler FFT process, as a first phase frequency-domain signal;
   processing each of the second reflected radar signals, by performing the Doppler FFT process, as a second phase frequency-domain signal;
   respectively obtaining a response characteristic from the first phase frequency-domain signal and the second phase frequency-domain signal;
   processing each of the first reflected radar signals and each of the second reflected radar signals, by performing a range FFT process and a direction-finding process, to obtain range information corresponding to each of the plurality of to-be-monitored objects;
   distinguishing the response characteristic of the first phase frequency-domain signal as an identification and distinguishing the response characteristic of the second phase frequency-domain signal as a physiological information; and
   labelling each piece of physiological information according to the range information and identification information, wherein the identification information is a time-varying frequency.

2. The physiological information monitoring and identification method according to claim 1, wherein the range information comprises distance information or orientation information.

3. The physiological information monitoring and identification method according to claim 1, further comprising:
   in response to the response characteristic being the identification information, determining that the to-be-monitored object associated with the identification information is the response device.

4. The physiological information monitoring and identification method according to claim 3, wherein the identification information is a vibration frequency of the response device or a change in a radar cross section of the response device.

5. The physiological information monitoring and identification method according to claim 1, further comprising:
   in response to the response characteristic being the physiological information, determining that the to-be-monitored object associated with the physiological information is the living body, and identifying the response characteristic as the physiological information of the living body.

6. The physiological information monitoring and identification method according to claim 5, further comprising: in response to the response characteristic being the identification information, determining that the to-be-monitored object associated with the identification information is the response device; wherein
   the step of labelling each piece of physiological information according to the range information and the identification information comprises:
   determining whether the range information of each of the living bodies matches the range information of each of the response devices; and
   in response to the range information of a specific living body matching the range information of a specific response device, labelling the physiological information of the specific living body by using the identification information of the specific response device.

7. The physiological information monitoring and identification method according to claim 1, wherein each of the incident radar signals is a frequency modulated radar signal.

8. The physiological information monitoring and identification method according to claim 1, wherein the response device includes a vibration unit and a driving unit, the driving unit controls the vibration unit to vibrate at a vibration frequency, the vibration unit has a reflecting surface, the reflecting surface includes a plurality of corner reflectors arranged adjacent to each other.

9. The physiological information monitoring and identification method according to claim 1, wherein the response device includes an active backscatter transponder, the backscatter transponder includes an antenna, matching networks, a low noise amplifier, a resonator, a phase shifter, a power amplifier driver, a power amplifier and a signal generator, the antenna receives each of the incident radar signals, the matching networks is for impedance matching, a received incident radar signal is processed by the low noise amplifier to resonate with the resonator, and is then amplified through the power amplifier driver and the power amplifier after phase compensation by the phase shifter, the signal generator generates a control signal for switching the power amplifier at a modulation frequency, so as to transmit the signal amplified by the power amplifier as the first reflected radar signal through the antenna.

10. A radar signal processing method for monitoring and identifying characterization information of a plurality of to-be-monitored objects, comprising:
    receiving at least one piece of first radar digital monitoring data corresponding to at least one response device in a plurality of to-be-monitored objects, at least one piece of second radar digital monitoring data corresponding to at least one living body in the plurality of to-be-monitored objects and at least one piece of third radar digital monitoring data corresponding to at least one moving object in the plurality of to-be-monitored objects;
    processing each piece of the first radar digital monitoring data, by performing a Doppler FFT process, as a first phase frequency phase-domain signal;
    processing each piece of the second radar digital monitoring data, by performing the Doppler FFT process, as a second phase frequency phase-domain signal;
    processing each piece of the third radar digital monitoring data, by performing the Doppler FFT process, as a third phase frequency phase-domain signal;
    respectively obtaining a response characteristic from the first phase frequency-domain signal, the second phase frequency-domain signal and the third phase frequency-domain signal;
    processing each piece of the first radar digital monitoring data, each piece of the second radar digital monitoring data and each piece of the third radar digital monitoring data, by performing a range FFT process and a direction-finding process, to obtain range information corresponding to each of the plurality of to-be-monitored objects;

distinguishing the response characteristic of the first phase frequency-domain signal as an identification and distinguishing the response characteristics of the second phase frequency-domain signal and the third phase frequency-domain signal as characterization information; and labelling each piece of characterization information according to the range information and identification information, wherein the identification information is a time-varying frequency.

11. The radar signal processing method according to claim 10, wherein the range information comprises distance information or orientation information.

12. The radar signal processing method according to claim 10, further comprising:
in response to the response characteristic being the identification information, determining that the to-be-monitored object associated with the identification information is the response device.

13. The radar signal processing method according to claim 12, wherein the identification information is a vibration frequency of the response device or a change in a radar cross section of the response device.

14. The radar signal processing method according to claim 10, further comprising:
in response to the response characteristic being the characterization information, further distinguishing the characterization information of the second phase frequency-domain signal as physiological information; and
in response to the response characteristic being the physiological information, determining that the to-be-monitored object associated with the physiological information is the living body, and identifying the response characteristic as the physiological information of the living body.

15. The radar signal processing method according to claim 10, further comprising:
in response to the response characteristic being the characterization information, further distinguishing the characterization information of the third phase frequency-domain signal as speed information; and
in response to the response characteristic being the speed information, determining that the to-be-monitored object associated with the speed information is the moving object and identifying the response characteristic as the speed information of the moving object.

16. The radar signal processing method according to claim 14, further comprising: in response to the response characteristic being the identification information, determining that the to-be-monitored object associated with the identification information is the response device; wherein
the step of labelling each piece of characterization information according to the range information and the identification information comprises:
determining whether the range information of each of the living bodies matches the range information of each of the response devices; and
in response to the range information of a specific living body matching the range information of a specific response device, labelling the physiological information of the specific living body by using the identification information of the specific response device.

17. The radar signal processing method according to claim 10, wherein the response device includes a vibration unit and a driving unit, the driving unit controls the vibration unit to vibrate at a vibration frequency, the vibration unit has a reflecting surface, the reflecting surface includes a plurality of corner reflectors arranged adjacent to each other.

18. The radar signal processing method according to claim 10, wherein the response device includes an active backscatter transponder, the backscatter transponder includes an antenna, matching networks, a low noise amplifier, a resonator, a phase shifter, a power amplifier driver, a power amplifier and a signal generator, the antenna receives an incident radar signal, the matching networks is for impedance matching, the incident radar signal is processed by the low noise amplifier to resonate with the resonator, and is then amplified through the power amplifier driver and the power amplifier after phase compensation by the phase shifter, the signal generator generates a control signal for switching the power amplifier at a modulation frequency, so as to transmit the signal amplified by the power amplifier as the first radar digital monitoring data through the antenna.

19. A physiological information monitoring radar, comprising:
a transceiver configured to transmit a plurality of incident radar signals to a plurality of to-be-monitored objects of a field and receive a first reflected radar signal corresponding to each of the response devices of the field and a second reflected radar signal corresponding to each of the living bodies of the field, wherein the to-be-monitored objects includes at least one response device and at least one living body; and
a signal processing module configured to process each of the first reflected radar signals, by performing a Doppler FFT process, as a first phase frequency-domain signal, process each of the second reflected radar signals, by performing the Doppler FFT process, as a second phase frequency-domain signal, respectively obtain a response characteristic from the first phase frequency-domain signal and the second phase frequency-domain signal, process each of the first reflected radar signals and each of the second reflected radar signals, by performing a range FFT process and a direction-finding process, to obtain range information corresponding to each of the plurality of to-be-monitored objects, distinguish the response characteristic of the first phase frequency-domain signal as an identification, distinguish the response characteristic of the second phase frequency-domain signal as a physiological information, and label each piece of physiological information according to the range information and identification information, wherein the identification information is a time-varying frequency.

20. The physiological information monitoring radar according to claim 19, wherein the range information comprises distance information or orientation information.

21. The physiological information monitoring radar according to claim 19, wherein in response to the response characteristic being the identification information, the signal processing module determines that the to-be-monitored object associated with the identification information is the response device.

22. The physiological information monitoring radar according to claim 21, wherein the identification information is a vibration frequency of the response device or a change in a radar cross section of the response device.

23. The physiological information monitoring radar according to claim 19, wherein in response to the response characteristic being the physiological information, the signal processing module determines that the to-be-monitored object associated with the physiological information is the living body, and identifies the response characteristic as the physiological information of the living body.

24. The physiological information monitoring radar according to claim 23, wherein in response to the response characteristic being the identification information, the signal processing module determines that the to-be-monitored object associated with the identification information is the response device and determines whether the range information of each of the living bodies matches the range information of each of the response devices, and in response to the range information of a specific living body matching the range information of a specific response device, the signal processing module labels the physiological information of the specific living body by using the identification information of the specific response device.

25. The physiological information monitoring radar according to claim 19, wherein the response device includes a vibration unit and a driving unit, the driving unit controls the vibration unit to vibrate at a vibration frequency, the vibration unit has a reflecting surface, the reflecting surface includes a plurality of corner reflectors arranged adjacent to each other.

26. The physiological information monitoring radar according to claim 19, wherein the response device includes an active backscatter transponder, the backscatter transponder includes an antenna, matching networks, a low noise amplifier, a resonator, a phase shifter, a power amplifier driver, a power amplifier and a signal generator, the antenna receives each of the incident radar signals, the matching networks is for impedance matching, a received incident radar signal is processed by the low noise amplifier to resonate with the resonator, and is then amplified through the power amplifier driver and the power amplifier after phase compensation by the phase shifter, the signal generator generates a control signal for switching the power amplifier at a modulation frequency, so as to transmit the signal amplified by the power amplifier as the first reflected radar signal through the antenna.

* * * * *